US012310556B2

(12) United States Patent
Dhaliwal et al.

(10) Patent No.: US 12,310,556 B2
(45) Date of Patent: May 27, 2025

(54) IMAGING SYSTEM AND METHOD

(71) Applicant: The University Court of the University of Edinburgh, Edinburgh (GB)

(72) Inventors: Kevin Dhaliwal, Edinburgh (GB); Michael G. Tanner, Edinburgh (GB); Robert R. Thomson, Edinburgh (GB)

(73) Assignee: The University Court of the University of Edinburgh, Edinburgh (GB)

( * ) Notice: Subject to any disclaimer, the term of this patent is extended or adjusted under 35 U.S.C. 154(b) by 901 days.

(21) Appl. No.: 16/960,856

(22) PCT Filed: Jan. 9, 2019

(86) PCT No.: PCT/GB2019/050051
§ 371 (c)(1),
(2) Date: Jul. 8, 2020

(87) PCT Pub. No.: WO2019/138220
PCT Pub. Date: Jul. 18, 2019

(65) Prior Publication Data
US 2021/0063722 A1 Mar. 4, 2021

(30) Foreign Application Priority Data
Jan. 9, 2018 (GB) ..................... 1800340

(51) Int. Cl.
*A61B 1/00* (2006.01)
*A61B 1/06* (2006.01)
(Continued)

(52) U.S. Cl.
CPC ............ *A61B 1/00165* (2013.01); *A61B 1/06* (2013.01); *A61B 1/07* (2013.01); *G02B 23/2469* (2013.01)

(58) Field of Classification Search
CPC ......... A61B 1/00165; A61B 1/06; A61B 1/07; G02B 23/2469
See application file for complete search history.

(56) References Cited

U.S. PATENT DOCUMENTS

| 5,017,771 A | 5/1991 | Bartholomew et al. |
| 5,696,563 A | 12/1997 | Rosenberg |
| (Continued) | | |

FOREIGN PATENT DOCUMENTS

| JP | 2005074188 A | 3/2005 |
| JP | 2006521860 A | 9/2006 |
| (Continued) | | |

OTHER PUBLICATIONS

International Preliminary Report on Patentability for PCT Application No. PCT/GB2019/050051, dated Jul. 14, 2020.
(Continued)

*Primary Examiner* — Timothy J Neal
*Assistant Examiner* — William B Chou
(74) *Attorney, Agent, or Firm* — Troutman Pepper Locke LLP; Christopher J. Capelli

(57) ABSTRACT

A system comprises a medical device configured to be positioned at least partially within a scattering medium, the medical device comprising at least one optical fibre or other waveguide having a plurality of light-emitting regions arranged along at least part of the length of the at least one optical fibre or other waveguide; a pulsed light source configured to transmit pulsed light into a proximal end of the at least one optical fibre or other waveguide, such that the pulsed light is guided along the at least one optical fibre or other waveguide to the light-emitting regions and emitted by the light-emitting regions into the scattering medium; at least one detector configured to receive photons of the pulsed light that have passed through the scattering medium;
(Continued)

and a processor configured to: select signals corresponding to at least some of the received photons; determine a respective location of each of the light-emitting regions based on the selected signals; and determine a path of at least part of the medical device based on the determined locations.

23 Claims, 4 Drawing Sheets

(51) Int. Cl.
    *A61B 1/07* (2006.01)
    *G02B 23/24* (2006.01)

(56) References Cited

U.S. PATENT DOCUMENTS

| | | | |
|---|---|---|---|
| 5,696,863 | A | 12/1997 | Kleinerman |
| 5,746,210 | A | 5/1998 | Benaron et al. |
| 2004/0078039 | A1 | 4/2004 | Michelson |
| 2008/0039715 | A1 | 2/2008 | Wilson et al. |
| 2008/0212082 | A1* | 9/2008 | Froggatt ............ G02B 6/02042 356/73.1 |
| 2010/0210952 | A1* | 8/2010 | Taira ...................... A61B 1/043 250/214 LA |
| 2011/0015521 | A1 | 1/2011 | Faul |
| 2015/0080867 | A1 | 3/2015 | Neuberger et al. |
| 2016/0266054 | A1* | 9/2016 | Cao ......................... G01T 1/247 |
| 2017/0255337 | A1 | 9/2017 | Drumm |
| 2017/0307439 | A1* | 10/2017 | Caucci .................. G01J 1/0414 |
| 2019/0298158 | A1* | 10/2019 | Dhaliwal .................. G01S 5/14 |

FOREIGN PATENT DOCUMENTS

| | | |
|---|---|---|
| JP | 2010528818 A | 8/2010 |
| JP | 2011200341 A | 10/2011 |
| JP | 2015077336 A | 4/2015 |
| JP | 2017500899 A | 1/2017 |
| WO | WO-2004078039 A1 | 9/2004 |
| WO | WO-2017174998 | 10/2017 |

OTHER PUBLICATIONS

International Search Report and Written Opinion for PCT Application No. PCT/GB2019/050051, dated Mar. 28, 2019.
Office Action from the European Patent Office for European Patent Application No. EP19700990.5, dated Feb. 27, 2023.
Office Action from the Japanese Patent Office for Japanese Patent No. JP2020537649, dated Oct. 18, 2022.
Office Action from the Chinese Patent Office for Chinese Application No. CN201980007699.5, dated Nov. 15, 2023.

* cited by examiner

IMAGING SYSTEM AND METHOD

This application is the U.S. National Stage of PCT International Application No. PCT/GB2019/050051, filed Jan. 9, 2019, which claims priority from Application GB1800340.0 filed on Jan. 9, 2018 in the United Kingdom. The entire disclosures of these applications are incorporated herein by reference in their entirety.

FIELD

The present invention relates to a system and method for determining a location of a medical device that is positioned inside a scattering medium, for example inside human or animal tissue.

BACKGROUND

Optical fibre based endoscopes are increasingly used for imaging and sensing internal to the human body. While bulk endoscopes often can be guided to particular regions of the internal organs through a steering mechanism, narrow optical fibre endoscopes may extend beyond the reach of the conventional system, having been pushed out of the working channel of the bulk endoscope. Alternatively, narrow fibre based endoscopes may be inserted without the use of any guided bulk endoscope at all.

In some scenarios, the final location of the endoscope may be approximated from knowledge of the insertion of the bulk endoscope, manual feel by the clinician, and/or visible structures in the very limited (for example, less than 1 mm) field of view of a fibre-based endoscope imaging system. In some circumstances, stereotactic techniques may be used to estimate the location of a fibre endoscope tip. X-ray or electromagnetic technologies may be used to view a metal end tip that may be on the end of the endoscope. However, X-ray or electromagnetic technologies may be expensive and/or require bulky apparatus. Furthermore, using X-rays to determine the location of the endoscope may expose a patient to unwanted radiation.

It is known to provide nutrition to patients using enteral feeding tubes, for example nasogastric (NG) tubes. Typically, NG tubes are placed blindly. For example, the process of insertion of the NG tube may take place without any imaging process being performed during the insertion. Subsequently, X-ray screening may be used to confirm position of the NG tube.

In some circumstances, misplacement of an enteral tube may occur. Various issues may arise from misplacement of an enteral tube, for example a nasogastric tube. A misplaced enteral tube may result in, for example, direct feeding into the lung or feeding into the oesophagus and subsequent aspiration pneumonia. Death or disability may result from pulmonary complications.

Feeding regimes using an NG tube may be continuous or intermittent. In general, the position of the distal end of an NG tube is checked prior to feeding. At present, aspiration of fluid and pH indicator strips are used. Fluid may be aspirated from the NG tube (for example, using a syringe) and the aspirated fluid may be tested using a pH indicator strip to determine the acidity of the aspirated fluid. A low pH (for example a pH of 4 of less) may be considered to indicate that the NG tube has been correctly placed. However, in some circumstances, the pH of the aspirated fluid may be confounded by concomitant use of antacids, other drugs or test indicator failure.

Thoracic X-rays may be used to check position of the NG tube. However, thoracic X-rays are often difficult to interpret. Thoracic X-rays require use of ionising radiation. Thoracic X-rays typically provide static images. Thoracic X-rays may require either the movement of the patient to a radiology department or a portable radiograph.

Current practice may be considered to be suboptimal. Numerous deaths and complications continue to occur due to misplacement of enteral tubes.

SUMMARY

In a first aspect, there is provided a system comprising: a medical device configured to be positioned at least partially within a scattering medium, the medical device comprising at least one optical fibre or other waveguide having a plurality of light-emitting regions arranged along at least part of the length of the at least one optical fibre or other waveguide; a pulsed light source configured to transmit pulsed light into a proximal end of the at least one optical fibre or other waveguide, such that the pulsed light is guided along the at least one optical fibre or other waveguide to the light-emitting regions and emitted by the light-emitting regions into the scattering medium; at least one detector configured to receive photons of the pulsed light that have passed through the scattering medium; and a processor configured to: select signals corresponding to at least some of the received photons; determine a respective location of each of the light-emitting regions based on the selected signals; and determine a path of at least part of the medical device based on the determined locations.

The scattering medium may comprise at least part of a body, which may be the body of a human or animal subject, for example a patient. The scattering medium may comprise tissue and/or fluids.

The medical device may comprise an endoscope. The medical device may comprise a tube. The tube may comprise an enteral tube, for example a nasogastric tube.

Determining a path of the at least part of the medical device may enable a clinician to determine a placement of the medical device. For example, the clinician may determine whether an endoscope or enteral tube has been misplaced during insertion. Misplacement events may be reduced, which may reduce the incidence of consequences of misplacement such as aspiration pneumonia.

Determining locations of the light-emitting regions by providing pulsed light through the at least one optical fibre or other waveguide may allow the path of the at least part of the medical device to be determined without using other methods that may expose a patient or other subject to unwanted radiation. For example, it may be desirable to minimise the use of ionising radiation in the case of children. Movement of the medical device over time may be determined and/or the positioning of the medical device may be checked without repeatedly or continuously exposing the patient to ionising radiation.

Determining locations of the light-emitting regions by providing pulsed light through the at least one optical fibre or other waveguide may allow the path of the at least part of the medical device to be determined without taking a patient (who may be frail) to an X-ray machine, or bringing a portable X-ray machine to the patient.

The light-emitting regions may be localised. The light-emitting regions may act as point sources. The determining of the respective location of each of the light-emitting regions may comprise considering the light-emitting regions to be point sources.

The light-emitting regions may be regularly spaced along the length of at least part of the at least one optical fibre or other waveguide. The spacing of the light-emitting regions may be uniform. The light-emitting regions may be separated by substantially non-light-emitting regions of the at least one optical fibre or other waveguide.

The light-emitting regions may be more densely arranged in a region of interest of the medical device. The region of the interest may be considered to be a critical region. The region of interest may be positioned at or near the distal end of the medical device. In some circumstances, there may be less certainty about placement of the distal end of the medical device than of the proximal end. Providing a greater density of light-emitting regions near the distal end may allow the location of the distal end to be better determined.

A spacing between adjacent light-emitting regions along the length of the at least one optical fibre or other waveguide may be at least 0.1 cm, optionally at least 0.5 cm, further optionally at least 1 cm. A spacing between adjacent light-emitting regions along the length of the at least one optical fibre or other waveguide may be less than 5 cm, optionally less than 2 cm, further optionally less than 1 cm.

The at least one optical fibre may comprise a plurality of optical fibres. Each of the light-emitting regions may comprise a tip of a respective one of the plurality of optical fibres.

Each of the light-emitting regions may comprise a region in which at least one physical property of a core and/or cladding of the at least one optical fibre or other waveguide is modified such that light is emitted from the light-emitting region into the scattering medium.

Each of the light-emitting regions may comprise at least one of a long-period fibre Bragg grating, a tilted fibre Bragg grating, a region of core damage. Each of the light-emitting regions may be configured to shift a wavelength of the pulsed light. Each of the light-emitting regions may be configured to shift a wavelength of the pulsed light by a respective value amount, such that different ones of the light-emitting regions emit light having different wavelengths.

Each of the light-emitting regions may be angled to direct light outwards from the medical device. Each of the light-emitting regions may be modified to direct light outwards from the medical device.

Different ones of the light-emitting regions may be configured to transmit and/or scatter different wavelengths of light.

Each of the light-emitting regions may comprise a scattering material. At least one property of the core and/or cladding may be configured to scatter light into the scattering medium. The scatting material may be configured to scatter light in a direction substantially perpendicular to the length of the medical device.

At least one property of a material of the medical device may be configured to scatter light into the scattering medium, for example a property of a material of a tube, sheath or coating.

The at least one optical fibre or other waveguide may be formed from glass. The at least one optical fibre or other waveguide may be formed from plastic. The at least one optical fibre or other waveguide may be formed from silica.

The or each optical fibre may have commercially standard dimensions. The or each optical fibre may have a core diameter of around 10 µm. The or each optical fibre may have a cladding diameter of around 125 µm. The or each optical fibre may have a plurality of cores, each having a core diameter of around 50 µm or around 62.5 µm, and a cladding diameter of around 125 µm. The or each optical fibre may comprise plastic fibre having a core diameter of around 1 mm.

The or each optical fibre may have a core diameter that is greater than 1 µm, optionally greater than 3 µm, further optionally greater than 5 µm, further optionally greater than 10 µm, further optionally greater than 50 µm. The or each optical fibre may have a core diameter that is less than 1 mm, optionally less than 200 µm, optionally less than 100 µm, further optionally less than 50 µm, further optionally less than 20 µm, further optionally less than 10 µm, further optionally less than 5 µm. The or each optical fibre may have a cladding diameter than is greater than 50 µm, optionally greater than 100 µm, further optionally greater than 500 µm. The or each optical fibre may have a cladding diameter than is less than 1000 µm, optionally less than 500 µm, further optionally less than 200 µm.

The at least one optical fibre or other waveguide may comprise a plurality of optical fibres or other waveguides. Each light-emitting region may be positioned at the tip of a respective one of the optical fibres or other waveguides.

The plurality of optical fibres or other waveguides may be packaged together, for example in a sheath. The plurality of optical fibres may be packaged together to form a composite fibre bundle. The plurality of optical fibres or other waveguides may comprise at least 10 optical fibres or other waveguides, optionally at least 20, further optionally at least 50, further optionally at least 100.

The medical device may comprise a tube. The composite fibre bundle may be positioned within a lumen of the tube. The composite fibre bundle may be integrated into tubing material of the tube.

The plurality of optical fibres or other waveguides may have different lengths. The plurality of optical fibres or other waveguides may be arranged such that proximal ends of the optical fibres are aligned. The plurality of optical fibres or other waveguides may be arranged such that distal ends of the optical fibres or other waveguides are spaced along the length of the at least part of the medical device.

Each of the light-emitting regions may comprise a modification of a respective one of the plurality of optical fibres or other waveguides. The optical fibres may be modified before being packaged together.

The plurality of light-emitting regions may be provided along at least part of the length of a single optical fibre or other waveguide. The light-emitting regions may be provided along the length of a single optical fibre core. Each of the light-emitting regions may comprise a respective modification of the optical fibre core.

The plurality of light-emitting regions may be provided on multiple cores of a multicore optical fibre. Each of the light-emitting regions may comprise a modification of a respective core of the multicore optical fibre.

The cores may comprise multiple subsets of cores, wherein for each subset, the cores in that subset have corresponding light-emitting regions. Each of the cores in the subset may have light-emitting regions in the same locations along the length of the multicore optical fibre as other cores in that subset.

The cores of the multicore fibre may be separated in the cross-sectional plane of the multicore fibre by a separation distance that is greater than a diameter of each core. The cores may be separated in the cross-sectional plane of the multicore fibre by a separation distance that is similar to a diameter of each core. The separation distance may be less than 100 µm, optionally less than 50 µm, further optionally less than 20 µm, further optionally less than 10 µm. The separation distance may be greater than 1 μm, optionally greater than 10 μm, further optionally greater than 20 μm, further optionally greater than 50 μm.

The medical device may comprise a tube. The medical device may comprise an enteral tube, optionally a nasogastric tube. The at least one optical fibre or other waveguide may be positioned within a lumen of the tube. The at least one optical fibre or other waveguide may be integrated into tubing material of the tube.

The tube may comprise at least two lumens. The at least one optical fibre or other waveguide may be positioned in a first one of the at least two lumens. A second one of the at least two lumens may be configured to supply liquid, for example a feeding liquid. The second one of the lumens may be configured to supply a liquid to and/or to obtain a liquid from a human or animal subject.

The at least one detector may be positioned outside the scattering medium. The selecting of the signals may be based on a time of arrival of the received photons at the at least one detector. By selecting signals based on a time of arrival, signals may be selected that are representative of photons that have undergone no scattering or a lesser amount of scattering than the majority of photons. Signals may be selected that are representative of photons that have undergone a degree of scattering that does not substantially degrade an amount of location information that is provided by the photons. Signals may be selected that are representative of photons that have undergone a degree of scattering that does not degrade the amount of location information that is provided by the photons beyond useful limits. Location information may be provided by each photon. For each photon, location information provided by that photon may comprise information about a location from which the photon emitted.

Location information may be provided by each of a plurality of collections of photons. A collection of photons may comprise photons collected for a particular time interval in a particular detector or detector element. For each collection of photons, location information provided by that collection of photons may comprise information about a location from which the collection of photons was emitted.

The location may comprise a location on the optical fibre or other waveguide. The location may comprise a location of a light-emitting region from which the photon was emitted. The location may comprise a location of a light-emitting region from which the collection of photons were omitted. The location information provided by the photons may comprise information about locations of the plurality of light-emitting regions.

Signals may be selected that are representative of photons that have been scattered substantially towards the at least one detector. Such signals may provide better location of the light-emitting regions than signals that are not selected based on time of arrival.

The determining of the location of each of the light-emitting regions based on the selected signals may comprise forming at least one image using the selected signals, and determining the location of each of the light-emitting regions based on the at least one image.

The at least one image may comprises a respective image for each of the light-emitting regions. The determining of the location of each light transmission feature may be based on the image for that light transmission feature.

Each location may be determined automatically. Each location may be determined manually. Each location may be determined by processing the image, or a respective one of the images, using image processing techniques. Each location may be determined by finding a part of the image, or a respective one of the images, having high intensity, for example a pixel of the image having a maximum intensity.

The selecting may comprise selecting signals corresponding to ballistic photons. Ballistic photons may comprise photons that have undergone no scattering in the scattering medium and/or photons that have undergone a small number of scattering events compared to the majority of photons. Ballistic photons may comprise the first photons of the pulsed light to be received at the at least one detector. Ballistic photons may comprise photons that are received within a first time bin.

The selecting may comprise selecting signals corresponding to snake photons. Snake photons may comprise photons that are later to arrive than ballistic photons, but that retain some location information. Snake photons may comprise photons that have been scattered along a more direct path towards the at least one detector.

For each snake photon, location information provided by that photon may comprise information about a location from which the photon was emitted. For each collection of snake photons, location information provided by that snake collection of snake photons may comprise information about a location from which the collection of snake photons was emitted.

The location may comprise a location on the optical fibre or other waveguide. The location may comprise a location of a light-emitting region from which the photon was emitted. The location may comprise a location of a light-emitting region from which the collection of photons was emitted. The location information provided by the snake photons may comprise information about locations of the plurality of light-emitting regions.

For each photon, a time of arrival for the photon may be determined by determining a difference between a time at which the photon was received at the at least one detector and a time at which a pulse of light was emitted by the pulsed light source, thereby triggering emission of the photon from the optical fibre or other waveguide.

The selecting of the signals may comprise selecting signals having a time of arrival below a threshold value. The threshold value may be expressed relative to a shortest detected time of arrival. The selecting of the signals may comprise selecting signals arriving no more than 10 nanoseconds after the shortest detected time of arrival, optionally no more than 5 nanoseconds, further optionally no more than 2 nanoseconds, further optionally no more than 1 nanosecond. The selecting of the signals may comprise selecting signals arriving no more than 500 picoseconds after the shortest detected time of arrival, optionally no more than 100 picoseconds, further optionally no more than 50 picoseconds.

The selecting of the signals may comprise selecting signals having a time of arrival within a time interval. The selecting of the signals may comprise selecting signals within one or more time bins.

The selecting of the signals may comprise selecting a first set of signals having a time of arrival in a first time bin; selecting a second set of signals having a time of arrival in a second time bin; and comparing the first set of signals with the second set of signals.

The first time bin may comprise the first 50 picoseconds after the shortest detected time of arrival. The second time bin may comprise the next 50 picoseconds after the first time bin.

The first time bin may comprise the first 100 picoseconds after the shortest detected time of arrival. The second time bin may comprise the next 100 picoseconds after the first time bin.

The selecting of the signals may comprise selecting a first set of signals having a time of arrival below a first threshold value; selecting a second set of signals having a time of arrival above the first threshold value but below a second threshold value; and comparing the first set of signals with the second set of signals. The selecting of the signals may comprise selecting signals between many threshold values, and comparing those signals. The selecting of the signals may comprise selecting multiple sets of signals, each set of signals comprising signals having a time of arrival between different threshold values, and comparing at least some of the multiple sets of signals to each other.

The selecting of the signals may comprise selecting multiple sets of signals, each set of signals comprising signals having a time of arrival with a respective time bin. The time bins may comprise 50 picosecond time bins. The time bins may comprise 100 picoseconds. The multiple sets of signals may comprise signals within a total range of time of arrival of 1 nanosecond. The multiple sets of signals may comprise signals within a total range of time of arrival of 5 nanoseconds.

The position of the at least one detector and/or the incident position of the light may be varied to build up an image by scanning the light across the scanning medium, for example across a patient.

The determining of the path of the at least part of the medical device may comprise applying shape-based image processing techniques. An expected shape of the medical device and/or an expected shape of the at least one optical fibre or other waveguide may be used in determining the path of the medical device. For example, it may be known that the medical device is continuous. It may be assumed that the medical device will assume a curved shape. A curvature of the medical device may be assumed to be within predetermined bounds.

The determining of the path of the at least part of the medical device may comprise using prior knowledge of a spacing of the light-emitting regions.

The pulsed light may comprise narrow band laser light. The pulsed light may comprise short pulse laser light. The pulsed light may comprise pulses having a length of less than 1000 ps, optionally less than 500 ps, further optionally less than 100 ps, further optionally less than 10 ps, further optionally less than 1 ps.

The pulsed light may be a pulse rate of up to 1000 MHz, optionally up to 200 MHz, further optionally up to 100 MHz, further optionally up to 10 MHz. The pulsed light may have a pulse rate between 10 and 100 MHz. The pulsed light may have a pulse rate of around 80 MHz. The pulsed light may have a pulse rate between 1 and 10 MHz.

The pulsed light source may have an illumination power of less than 100 mW, optionally less than 50 mW, optionally less than 20 mW, optionally less than 10 mW, optionally less than 1 mW.

The system may further comprise a filter configured to filter the received photons. The filter may be configured to transmit photons at a wavelength of the pulsed light. The filter may be configured to transmit photons at a wavelength of the pulsed light as shifted by at least one of the light-emitting regions.

The at least one detector may comprise a detector array. The at least one detector may comprise a scanning detector. The at least one detector may comprise a single-photon detector. The single-photon detector may comprise at least one SPAD (single photon avalanche diode). The at least one detector may comprise at least one of: an APD (avalanche photo diode detector), a streak camera, a time-gated intensified camera with a CCD detector array (ICCD), a photomultiplier tube (PMTs), a superconducting single photon detector.

The system may further comprise at least one focusing component, wherein the at least one focusing component is configured to focus the received photons onto the at least one detector. The at least one focusing component may comprise at least one lens.

The transmitting of the pulsed light into the scattering medium may comprise individually illuminating each of the light-emitting regions. Individually illuminating each of the light-emitting regions may comprise illuminating each of the light transmission feature in turn. Individually illuminating each of the light-emitting regions may comprise illuminating each of the light-emitting regions using a respective different wavelength. Individually illuminating each of the light-emitting regions may comprise individually illuminating each of a plurality of cores of the at least one optical fibre. Individually illuminating each of the light-emitting regions may comprise illuminating the at least one optical fibre or other waveguide using different wavelengths in turn, wherein each of the light-emitting regions is configured to transmit a selected one of the different wavelengths.

The transmitting of the pulsed light into the scattering medium may comprise illuminating a plurality of the light-emitting regions simultaneously. The transmitting of the pulsed light into the scattering medium may comprise illuminating all of the light-emitting regions simultaneously.

The determining of the locations of the light-emitting regions may be performed repeatedly. The determining of the locations of the light-emitting regions may be performed repeatedly while the at least part of the medical device is moved relative to the scattering medium. The moving of the medical device may be automated. The moving of the medical device may be performed in predetermined increments.

The medical device may comprise or form part of at least one medical instrument. The medical device may be co-located with at least one medical instrument.

The medical instrument may comprise at least one of an endoscope, a guide wire, a catheter, a catheter delivery system, a scalpel, an energy source for ablation or modification of tissue.

The processor may be further configured to determine a location of at least part of the medical instrument based on the determined path of the at least part of the medical device.

The medical device may be positioned at least partially inside a human or animal body. The determining of the path of the at least part of the medical device may comprise determining the path of the at least part of the medical device inside the human or animal body.

The medical device and/or medical instrument may be placed inside the human or animal body using an automated procedure. The determining of the path of the at least part of the medical device may comprise a verification of the automated procedure.

At least part of the medical device may be positioned inside a human or animal subject. The scattering medium may comprise tissue of at least one of: a lung, an upper gastrointestinal tract, a lower gastrointestinal tract, a urinary tract, bone tissue, organ tissue.

The at least part of the medical device may be positioned inside the oesophagus of the subject. The processor may be configured to use the determined path of the at least part of the medical device to determine a location of the tube inside the oesophagus of the subject.

The processor may be further configured to use the selected photons to determine a tissue type of at least part of the human or animal tissue. The determining of the tissue type of the at least part of the human or animal tissue may comprise determining whether the tissue is healthy or diseased. The determining of the tissue type may comprise determining a degree of scattering of the photons corresponding to the selected signals, and determining the tissue type based on the determined degree of scattering.

In a further aspect, which may be provided independently, there is provided a medical device configured to be positioned at least partially within a scattering medium, the medical device comprising at least one optical fibre or other waveguide having a plurality of light-emitting regions arranged along at least part of the length of the at least one optical fibre or other waveguide, such that light transmitted into a proximal end of the at least one optical fibre or other waveguide is guided along the at least one optical fibre or other waveguide to the light-emitting regions and emitted by the light-emitting regions.

In a further aspect, which may be provided independently, there is provided a method for determining a path of at least part of a medical device, the medical device comprising at least one optical fibre or other waveguide having a plurality of light-emitting regions arranged along at least part of the length of the at least one optical fibre. The method comprises positioning the medical device at least partially within a scattering medium; transmitting pulsed light into the at least one optical fibre or other waveguide, such that the pulsed light is guided along the at least one optical fibre or other waveguide to the light-emitting regions and emitted by the light-emitting regions into the scattering medium; receiving by at least one detector photons of the pulsed light that have passed through the scattering medium; selecting signals corresponding to at least some of the received photons; determining a respective location of each of the light-emitting regions based on the selected signals; and determining a path of at least part of the medical device based on the determined locations.

In a further aspect, which may be provided independently, there is provided a computer program product comprising computer-readable instructions that are executable by a processor to select signals corresponding to received photons of pulsed light that have passed through a scattering medium, to determine a respective location of each of plurality of light-emitting regions based on the selected signals, and to determine a path of a medical device based on the determined locations.

The scattering medium may comprise at least part of a body of a human or animal subject. The processor may be further configured to compare the determined location of the medical device to an expected anatomy of the subject.

The processor may be further configured to determine the expected anatomy of the subject. The determining of the expected anatomy may comprise obtaining at least one medical image of at least part of the body of the subject. The determining of the expected anatomy may comprise processing the at least one medical image to identify at least one anatomical structure. The at least one anatomical structure may comprise the oesophagus. The at least one anatomical structure may comprise the bronchi. The at least one anatomical structure may comprise a transpyloric plane of the subject. The at least one anatomical structure may comprise at least one intercostal space of the subject. The at least one anatomical structure may comprise at least one vertebra of the subject.

The comparing the location of the medical device to the expected anatomy of the subject may comprise determining a location of the medical device relative to the oesophagus and/or bronchi.

The comparing the location of the medical device to the expected anatomy of the subject may comprise overlaying a medical image of the subject and the determined location of the or each light transmission feature and/or the determined location of the medical device. The comparing the location of the medical device to the expected anatomy of the subject may comprise overlaying at least one anatomical marker and the determined location of the or each light transmission feature and/or the determined location of the medical device.

The processor may be configured to identify at least one anatomical feature in the medical image, and to use the identified at least one anatomical feature in the comparing of the location of the medical device to the expected anatomy of the subject.

The identifying of the at least one anatomical feature may comprise segmenting and/or labelling the at least one anatomical feature.

In a further aspect, which may be provided independently, there is provided a graphical user interface configured to display a location of each of a plurality of light-emitting regions based on selected signals, the signals corresponding to received photons of pulsed light that have passed through a scattering medium, and/or to display a path of a medical device that has been determined using the locations of the plurality of light-emitting regions.

In a further aspect, which may be provided independently, there is provided a system comprising: a medical device configured to be positioned at least partially within a scattering medium, the medical device comprising at least one optical fibre or other waveguide having a plurality of light-receiving regions arranged along at least part of the length of the at least one optical fibre or other waveguide; a pulsed light source external to the scattering medium and configured to transmit pulsed light into the scattering medium; at least one detector coupled to a proximal end of the at least one optical fibre or other waveguide, wherein the at least one detector is configured to receive photons of the pulsed light that have passed through the scattering medium and been received through the light-receiving regions and guided along the at least one optical fibre or other waveguide to the at least one detector; and a processor configured to: select signals corresponding to at least some of the received photons; determine a respective location of each of the light-receiving regions based on the selected signals; and determine a path of at least part of the medical device based on the determined locations.

The transmitting of the pulsed light into the scattering medium may comprise varying a position of the light source with respect to the scattering medium and/or varying an incident position of the pulsed light from the light source on the scattering medium.

In a further aspect, which may be provided independently, there is provided a method of forming a medical device, the method comprising providing at least one optical fibre or other waveguide, and fabricating in the at least one optical fibre or other waveguide a plurality of light-emitting regions arranged along at least part of the length of the at least one optical fibre or other waveguide.

The fabricating of the plurality of light-emitting regions may comprise using a laser, for example a femtosecond laser or UV laser. The forming of the plurality of light-emitting regions may comprise using UV light. Each of the plurality of light-emitting regions may comprise at least one of a long-period fibre Bragg grating, a tilted fibre Bragg grating, a region of core damage.

Different ones of the light-emitting regions may be fabricated such as to transmit and/or scatter different wavelengths of light.

The at least one optical fibre may comprise a single-core optical fibre. The fabricating of the light-emitting regions may comprise fabricating multiple light-emitting regions along the core of the single-core optical fibre.

The at least one optical fibre may comprise a multicore optical fibre. The fabricating of the light-emitting regions may comprise fabricating light-emitting regions on multiple cores of the multicore optical fibre.

In a further aspect, which may be provided independently, there is provided a method of forming a medical device, the method comprising providing at least one optical fibre or other waveguide, and fabricating in the at least one optical fibre or other waveguide a plurality of light-receiving regions arranged along at least part of the length of the at least one optical fibre or other waveguide.

In a further aspect, there is provided a system comprising: an enteral tube configured to be positioned at least partially inside the body of a human or animal subject. The enteral tube comprises or at least partially contains at least one optical fibre or other waveguide, the at least one optical fibre or other waveguide comprising at least one light-emitting region. The system further comprises a pulsed light source configured to transmit pulsed light into a proximal end of the at least one optical fibre or other waveguide, such that the pulsed light is guided along the at least one optical fibre or other waveguide to the light-emitting region or regions and emitted by the light-emitting region or regions into the body of the subject. The system further comprises at least one detector configured to receive photons of the pulsed light that have passed through the body of the subject; and a processor configured to: select signals corresponding to at least some of the received photons; determine a location of the or each light-emitting region based on the selected signals; and determine a location of the enteral tube based on the determined location or locations.

Determining a location of an enteral tube using the emission of light may reduce instances of misplacement. A clinician may be able to determine whether the enteral tube is correctly placed. The location of the enteral tube may be determined without subjecting the subject to radiation.

The enteral tube may comprise a nasogastric tube. The at least one optical fibre may be integrated into a wall of the enteral tube.

The at least one optical fibre or other waveguide may be at least partially contained within a lumen of the enteral tube.

The determining of the location of the or each light-emitting region may be performed repeatedly. The determining of the location of the or each light-emitting region may be performed repeatedly while the at least part of the enteral tube is moved relative to the body of the human or animal subject.

The determining of the location of the or each light-emitting region may be performed repeatedly while the at least one optical fibre or other waveguide is moved relative to the enteral tube. The moving of the at least one optical fibre or other waveguide relative to the enteral tube may be automated. The moving of the at least one optical fibre or other waveguide relative to the enteral tube may be performed in predetermined increments.

The processor may be further configured to compare the determined location of the enteral tube to an expected anatomy of the subject. The processor may be configured to repeatedly determine the location of the enteral tube over time and repeatedly compare the determined location of the enteral tube to the expected anatomy, for example to determine whether the enteral tube is being correctly inserted.

There may be provided a method, apparatus or system substantially as described herein with reference to the accompanying drawings.

Features in one aspect may be provided as features in any other aspect as appropriate. For example, features of a method may be provided as features of an apparatus and vice versa. Any feature or features in one aspect may be provided in combination with any suitable feature or features in any other aspect.

DETAILED DESCRIPTION

Embodiments of the invention are now described, by way of non-limiting example, and are illustrated in the following figures, in which.

It can be commonly observed that, in some circumstances, light may pass through tissue. For example, a bright white torch held against a hand or fingers may be observed as a red glow on an opposite surface of the hand or fingers. Embodiments of the present invention use light passing through tissue (or through any other suitable scattering medium) to determine a path of a medical device that is positioned inside that tissue (or other scattering medium).

Figure 1:
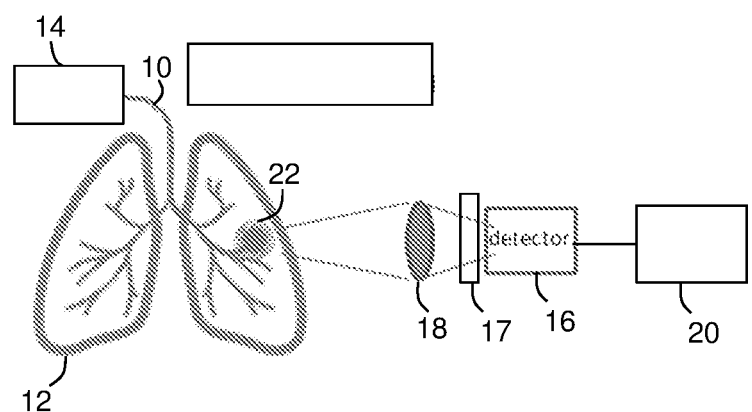
FIG. 1 is a schematic illustration of a fibre and detector setup in accordance with an embodiment.

An apparatus in accordance with an embodiment is illustrated schematically in FIG. 1. The apparatus comprises a medical device 10, light source 14, detector 16, filter 17, lens 18 and processor 20.

The light source 14 is coupled to the proximal end of the medical device 10 and is configured to deliver pulsed light into the medical device 10. In the present embodiment, the light source 14 is a narrow band short pulse laser.

The medical device 10 is configured to transmit light from the light source 14 to the distal end of the medical device 10. FIG. 1 shows the medical device 10 positioned inside the lung 12 of a patient. In other embodiments, the medical device 10 may be positioned inside a different part of a human or animal body, for example the gastrointestinal tract or urinary tract. In further embodiments, the medical device 10 may be positioned inside any suitable scattering medium. The scattering medium may be, for example, tissue, a body, or an organ. The scattering medium may be a gas. The scattering medium may be a liquid, for example a murky liquid. The scattering medium may be referred to as a sample, with at least the tip of the medical device 10 being positioned inside the sample.

The detector 16 (which may be referred to as a camera) is positioned outside the body of the patient. The detector 16 is configured to receive photons and generate an electrical signal corresponding to each received photon. In the present embodiment, the detector 16 is a detector array comprising a plurality of detector elements. The detector 16 is a time-resolved single photon imaging system. In this case, the time-resolved single photon imaging system comprises a 32×32 array of SPADs (single photon avalanche diodes). The time-resolved single photon imaging system operates by time-correlated single-photon counting (TCSPC). In other embodiments, any suitable time-resolved detector may be used. The time-resolved detector may be a time-resolved detector that is capable of detecting low levels of light, for example capable of detecting single photons. The time-resolved detector may comprise an APD (avalanche photo diode) detector or a streak camera. The time-resolved detector may comprise a time-gated intensified camera with a CCD detector array (ICCD). The time-resolved detector may comprise a plurality of photomultiplier tubes (PMTs) or superconducting single photon detectors. In some embodiments, multiple detectors 16 may be used. In some embodiments, a single element detector may be used in combination with an optical scanning system to create an image.

In the present embodiment, the detector 16 is mounted on an arm (not shown) which may be placed at any suitable position relative to the body of the patient. In other embodiments, any suitable mounting of the detector 16 may be used. For example, the detector 16 may be mounted on the ceiling of a room in which a procedure is to be performed in which the medical device 10 is to be positioned inside the patient, for example the ceiling of a hospital ward or operating theatre. In some embodiments, the detector 16 may be mounted on the head or body of the clinician, assistant or other user, to provide intuitive feedback to the clinician, assistant or other user.

Lens 18 is positioned between the detector 16 and the patient's body. The detector 16 and the lens 18 are arranged such that the detector 16 is in focus on the body of the patient. In other embodiments, an alternative focusing component may be used instead of the lens 18, or no focusing component may be used.

Filter 17 is positioned in front of the detector 16. In the present embodiment, filter 17 is positioned between the detector 16 and the lens 18. In the present embodiment, filter 17 is a narrow line pass filter. Filter 17 is configured to block any photons that are not within the spectral band of the laser source 14. In other embodiments, an alternative filter may be used, or no filter may be used.

The detector 16 is connected to a processor 20 which is configured to receive and analyse signals from the detector 16. The processor 20 may comprise any suitable processing device, for example a computing device such as a desktop PC, laptop or mobile device. Although in the present embodiment the detector 16 and processor 20 are separate components, in other embodiments the functions of the detector 16 and processor 20 may be combined in a single component. Functions described as being performed by the detector 16 may be performed by the processor 20, and vice versa.

Figure 2:
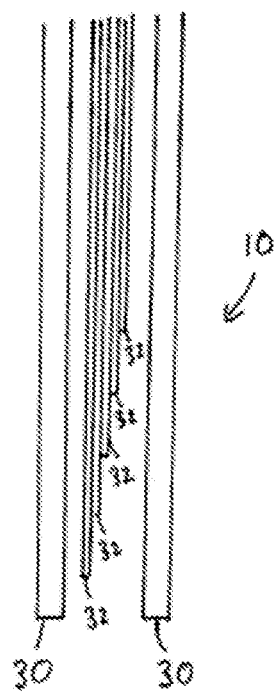
FIG. 2 is a schematic illustration of a distal end of a medical device in accordance with an embodiment.

FIG. 2 is a schematic diagram of the distal end of the medical device 10 of FIG. 1. FIG. 2 is a simplified diagram, and is not drawn to scale.

The medical device 10 of FIG. 2 comprises a catheter 30, which may also be referred to as a tube. A plurality of optical fibres 32 are each fed individually inside a lumen of the catheter 30 to form the medical device 10. Each of the optical fibres 32 is terminated at a different distance down the catheter, such that the distal end of each optical fibre 32 acts as a point-like source of light at a different point along the catheter 30. The tips of the optical fibres 32 may be described as termination points, light emitters, or light-emitting regions.

In the embodiment of FIG. 2, the spacing between the termination points of the optical fibres 32 is a uniform spacing of 1 cm. In other embodiments, the spacing of fibres may be closer along the length of the device. In further embodiments, the spacing of the termination points of the fibres may not be uniform. For example, the distribution of termination points along the length of the device may become denser as it approaches the tip of the device.

In the embodiment of FIG. 2, the individual fibres have standard dimensions. The individual fibres have a core diameter of around 10 µm and a cladding diameter of around 125 µm. In other embodiments, any suitable fibre dimensions may be used. The optical fibres may be formed of glass or of plastic.

For each of the optical fibres 32, the end of the optical fibre may be considered to act as a localised light source. The end of the optical fibre may be considered to act as a single point-like source of pulsed light. If the number of optical fibres is N, the method of FIG. 2 may be considered to allow the generation of N point-like sources of light. The N point-like sources of light are distributed along at least part of the length of the medical device 10. In some embodiments, the number of optical fibres N may be at least 10, at least 20, at least 50 or at least 100.

In the embodiment of FIG. 2, the tips of the optical fibres 32 are terminated such as to direct light outwards from the medical device 10. For example, a scattering element (not shown) may be positioned at the tip of each optical fibre 32 and/or the tips of the optical fibres 32 may be angled to direct light outwards from the medical device 10 (for example, out of the sides of the medical device 10).

In other embodiments, the optical fibres may be bundled or otherwise contained in a sheath, which may be referred to as a packaging sheath. The optical fibres may be coated with a coating. The material of the sheath or coating may be deliberately high in scattering to direct light out from the medical device 10.

In other embodiments, any medical device may be used which comprises at least one optical fibre. For example, an embodiment in which the medical device comprises a single optical fibre is described below with reference to FIG. 3, and an embodiment in which the optical device comprises a multicore optical fibre is described below with reference to FIG. 4.

We turn again to the embodiment of FIGS. 1 and 2. In operation, light emitted from each of the termination points of the optical fibres 32 is used to track the length of the optical fibre. Since the termination points are arranged along the length of the medical device 10, the locations of the termination points may be used to track the length of the optical fibre. It may be possible to locate an extended part of the medical device 10 instead of just a single point (for example, the tip).

A method of determining a location for a light emitter in a scattering medium using time-correlated single-photon counting (TCSPC) is described in Tanner et al (M. G. Tanner, T. R. Choudhary, T. H. Craven, B. Mills, M. Bradley, R. K. Henderson, K. Dhaliwal, and R. R. Thomson, "Ballistic and snake photon imaging for locating optical endomicroscopy fibres," Biomed. Opt. Express 8, 4077-4095 (2017)) and is summarised below. Tanner et al describes the locating of a point light at the tip of an optical fibre. The method described below applies the location method of Tanner et al to each of the termination points.

Photon transit timing is also discussed in, for example, L. Wang, P. P. Ho, C. Liu, G. Zhang, and R. R. Alfano, "Ballistic 2-d imaging through scattering walls using an ultrafast optical kerr gate.," Science 253, 769-71 (1991); V. Ntziachristos, "Going deeper than microscopy: the optical imaging frontier in biology.," Nat. Methods 7, 603-614 (2010); V. Gopal, S. Mujumdar, H. Ramachandran, and A. K. Sood, "Imaging in turbid media using quasi-ballistic photons," Opt. Commun. 170, 331-345 (1999); and A. Lyons, A. Boccolini, F. Tonolini, A. Repetti, Z. Chen, R. Henderson, Y. Wiaux, and D. Faccio, "Computational time-of-flight diffuse optical tomography," arXiv:1808.01135 (2018).

The medical device 10 is introduced into the lungs 12 of the patient, for example as part of an endoscopy procedure. In other embodiments, the medical device 10 may be introduced into any suitable anatomy. For example, the medical device may form part of an enteral feeding tube and may be introduced into the oesophagus.

Short pulsed (in the present embodiment, having a pulse length of <500 ps and pulse rate of 20 MHz) narrow band laser light is injected into a first one of the optical fibres 32 by light source 14. In other embodiments, any pulsed light with a repeatable leading edge may be used. In the present embodiment, the illumination power of the laser source 14 is a few mW, which is known to be safe in tissue. The wavelength of the laser source 14 may be chosen to be a wavelength that has low scattering and absorption in tissue.

In the embodiment of FIG. 2, the individual sources of light can be switched on and off at will from the proximal end.

The laser light is injected into the first one of the optical fibres 32 over a time period that may be seconds or minutes. Each pulse of laser light passes down the length of the optical fibre 32 and is emitted from the distal tip of the optical fibre 32 as a large number of photons (shown as light 22 in FIG. 1). The time of emission of the pulse of light from the distal tip of the optical fibre 10 may be designated as t=0. Only a small number of the photons emitted from the distal tip of the optical fibre 32 may escape from the body. Many of the photons emitted by the optical fibre 32 are absorbed in the tissue. Most of the photons that escape from the body (and therefore can be observed by the detector 16) may have undergone much scattering from the disordered tissue structures of the body. The time taken by each photon to travel through the tissue may be dependent on how many times the photon has been scattered while travelling through the tissue.

Photons that pass through the tissue and out of the body may comprise ballistic photons, snake photons, and/or highly scattered photons.

Ballistic photons may be photons that travel through a scattering medium in a straight line substantially without scattering. Such photons may be considered not to have collided with the atoms of the scattering medium, or to have undergone a very small number of scattering collisions. Ballistic photons may be substantially coherent.

Slightly scattered photons may be referred to as snake photons. Snake photons may be those that have undergone a small number of scattering events in the tissue (more than those designated as ballistic), but which still may provide useful location information. Snake photons may retain some degree of coherence. Snake photons may arrive slightly delayed from the ballistic photons.

Photons which experience a greater degree of scattering may be referred to as highly scattered photons, very scattered photons or randomly scattered photons.

The photons that pass out of the body may comprise ballistic photons, snake photons, and highly scattered photons. Some of the photons passing out of the body travel in the direction of the detector 16 and are focused by lens 18 onto the detector 16. Any photons that are not within the spectral band of the laser source 14 may be blocked by the narrow line pass filter 17 in front of the detector 16. Ballistic photons arrive first, followed by snake photons, followed by highly scattered photons.

In practice, the number of photons from each pulse that arrive at the detector 16 may be very small. In particular, only a small number of ballistic and/or snake photons may be obtained from each pulse. Therefore, photons from a large number of pulses are collected by detector 16 and the results are summed as described below.

The detector 16 converts each detected photon into an electrical signal. In the present embodiment, the detector 16 operates by time-correlated single-photon counting (TCSPC) in start-stop mode. There is synchronisation between the light source 14 and the detector 16 via an electrical connection. When the laser light source 14 creates a pulse of light, it also sends an electrical pulse to the detector 16. When the detector 16 receives the electrical pulse it starts timing. When the detector 16 observes a photon (for example, when a detector element of the detector array observes a photon) the detector stops timing. The electrical signal representing the detected photon includes a time of arrival that represents the difference between the time of transmission of the pulse and the time at which the photon arrives at the detector 16.

In other embodiments, the detector 16 starts timing when it detects a photon, and stops timing when it receives the next electrical pulse (reverse start-stop mode). Since the time between pulses is known, a time of arrival may be determined. In other embodiments, any suitable method of determining a time of arrival may be used.

In the present embodiment, the electrical signal representing the detected photon also includes a position. The position is determined based on which array element(s) of the 32×32 array detected the photon.

In other embodiments, any suitable method of determining the time of arrival and/or position of each detected photon may be used. The time of arrival and/or position of each photon may be represented by any suitable signal or combination of signals.

The electrical signals are passed to the processor 20. Since the time of arrival of each photon is determined relative to a time of transmission of its respective pulse, results can be combined across numerous pulses. The processor 20 combines the electrical signals by histogramming. In other embodiments, the processor 20 may combine the electrical signals in any suitable manner. In further embodiments, electrical signals may be combined in circuitry of the detector 16.

The processor 20 records photon arrivals in time bins, which in this embodiment are 50 ps time bins. In other embodiments, any suitable size of time bins may be used. The processor 20 selects the electrical signals for which the determined time of arrival is within a desired time bin, for example within the first 50 ps time bin. In other embodiments, the processor may select electrical signals in dependence on any suitable time threshold or thresholds. The selected electrical signals may correspond to only ballistic photons, or to both ballistic photons and snake photons, or to any photons reaching the detector sooner than more scattered photons.

In some embodiments, the processor 20 may select the electrical signals for which the determined time of arrival is no more than 100 ps, no more than 200 ps or no more than 500 ps. In other embodiments, the processor 20 may select the electrical signals for which the determined time of arrival is no more than 1 ns or no more than 5 ns. In other embodiments, the processor 20 may compare signals in different time bins. For example, the processor 20 may compare signals in a first 50 ps time bin to signals in a second 50 ps time bin. The processor 20 may compare signals in a first 100 ps time bin to signals in a second 100 ps time bin. The processor 20 may compare signals in multiple time bins, for example by comparing signals in every 50 ps time bin over a 1 ns or 5 ns interval. In some embodiments, multiple or varied timing windows may be used.

The processor 20 forms an image from the selected signals, which in this embodiment are the signals falling within the selected time bin. In the present embodiment, the image comprises one pixel for each element of the detector array 16. The detector array 16 comprises 32×32 elements, so the image formed is a 32×32 pixel image. The intensity of each pixel in the image represents the number of photons having a time of arrival within the selected time bin that was received by the corresponding array element during that time bin. Each of the detector elements of the detector array may detect light having a different angular origin relative to the detector array.

The processor 20 determines a location of the tip of the optical fibre 32 by processing the image formed from the selected signals. In the present embodiment, the processor 20 determines the location of the tip of the optical fibre 32 automatically using the intensities of the pixels of each image, which are representative of the numbers of photons received by each element of the detector array.

Each of the received photons provides information relating to the termination point from which it was emitted. In the present embodiment, collections of photon arrivals are considered when determining location information. A collection of photons may be a group of photons that falls within the same time bin and/or pixel. Each of the collections of received photons may provide location information relating to the termination point from which the photons in the collection of photons were emitted.

The location determined from the image is a location in a plane defined by the orientation of the detector array 16, which may be designated as the xy plane. In some embodiments, a location of the medical device 10 in z is also determined by using time of flight of photons received by the detector 16 (for example, the time of flight of the ballistic photons) to determine a distance between the detector 16 and the tip of the medical device 10.

The laser light is then injected into a second one of the optical fibres 32 and a location of the tip of the second optical fibre 32 is determined as described above. The injection of laser light into an optical fibre 32 and the determining of a position of the tip of that optical fibre 32 is repeated until a respective location has been determined for each of the optical fibre termination points.

In the present embodiment, the optical fibres 32 are illuminated individually, with only one optical fibre 32 illuminated at a time. In other embodiments, more than one optical fibre 32 may be illuminated. In some embodiments, all of the optical fibres 32 are illuminated at once.

The determined locations of the termination points are used to determine a path of the medical device 10. Determining a path of the medical device 10 may comprise determining a line or other elongate geometric structure that follows the longitudinal dimension of the medical device 10. The path may be determined for a portion of the medical device 10, for example a portion that is positioned inside the body of a patient.

By determining a path of the medical device, a clinician may obtain information about whether a medical device has been correctly placed, for example in the lungs or gastrointestinal tract. Various medical applications are described further below.

Any automatic or semi-automatic method may be used to determine the path of the medical device 10. In some embodiments, knowledge of the spacing between the termination points and/or the uniform spacing of the termination points is used in the determining of the path. For example, the processing of an image or images obtained from the transmitted light may take into account an expected spacing between light emitters.

In some embodiments, prior knowledge that the medical device 10 is an elongate device having gentle bends may allow advanced image processing techniques to be employed to reconstruct accurate images of the location of the fibre length. For example, image processing techniques may comprise a probabilistic atlas-based approach and/or optimisation of a restricted curve fit.

In some embodiments, a computer program is installed on the processor 20, which may comprise or form part of any suitable computing device. The computer program is configured to determine the location of the termination points and thereby to determine the path of the medical device 10 is installed on the processor 20. The computer program is configured to use the electrical signals that are representative of the received photons to determine the location of the termination points.

The computer program may be configured to display a graphical user interface. The graphical user interface may be displayed on a display screen. The graphical user interface may allow a user (for example, a clinician) to view the determined location of the termination points and/or the determined path of the medical device 10. By viewing the termination points and/or path, the user may obtain information about the position of the medical device 10. The graphical user interface may allow the user to input information, for example information about the subject, the medical device 10, or the procedure being performed. The graphical user interface may allow the user to control or adjust the method used to determine the location of the termination points and/or the path of the device.

In the embodiment described above with reference to FIG. 2, fibres 32 are individually inserted into the catheter 30 In other embodiments, fibres are co-packaged inside a tube or sheath. The tube or sheath is then inserted into a medical instrument (for example, an enteral tube or endoscope). In further embodiments, the medical instrument is supplied with the packaged fibres in place, then withdrawn after positioning. For example, in some embodiments, the packaged fibres are initially positioned within the working channel of a catheter. If left in place, the packaged fibres may block normal usage. Therefore, the packaged fibres are withdrawn from the working channel of the catheter after the catheter has been positioned within the body of the subject, and before the catheter is used. Similar considerations may apply to any embodiment in which at least one optical fibre is initially positioned within a medical instrument and then withdrawn.

In some embodiments, the medical tubing of the catheter is made of plastic, and the optical fibres are integrated into the plastic of the medical tubing during manufacture. In other embodiments, the fibres are bundled together with controlled tip spacing and coated to form a single composite fibre bundle. The single composite fibre bundle then placed within the medical device or tubing. In some embodiments, a composite fibre bundle is integrated into the plastic of medical tubing or a medical device during manufacture.

In some embodiments, the medical tubing contains two channels. One channel holds the optical fibres. The other channel is used for normal operation (for example, feeding, drug delivery and/or sample aspiration).

In the embodiment of FIG. 2, individual optical fibres are illuminated sequentially. In some embodiments, individual fibres are illuminated sequentially through use of an optical switch. An optical switch may be a switch that enables signals in optical fibres to be selectively switched from one fibre for another, for example as described in Federal Standard 1037C, Telecommunications: Glossary of Telecommunication Terms, Aug. 7, 1996.

In some embodiments, optical fibres are bundled together and are illuminated sequentially. Bundled fibres may be illuminated sequentially through controlled illumination patterns from a digital micromirror device.

In some embodiments, all optical fibres 32 of the medical device 10 of FIG. 2 are illuminated simultaneously. The simultaneous illumination of the proximal end results in emission at the distal ends of the optical fibres 32 that occurs in sequence from the shortest optical fibre 32 to the longest optical fibre 32, delayed by propagation along the length of the fibres.

The method outlined above with reference to FIG. 2 uses N fibres. The N fibres of FIG. 2 are co-packaged and carefully positioned into a clinically approved package.

Figure 3:
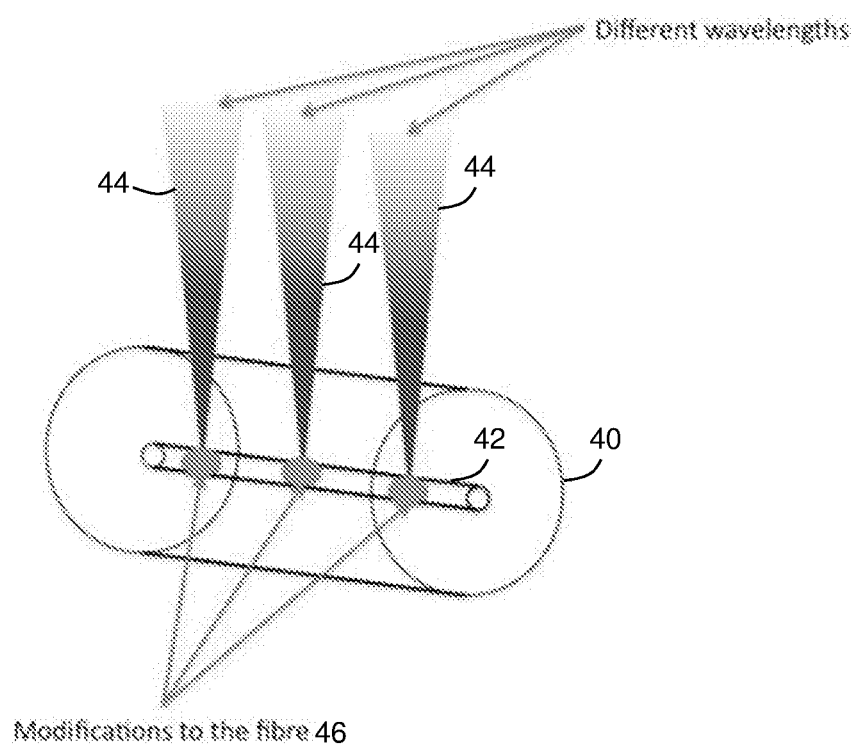
FIG. 3 is a schematic illustration of a section of a modified fibre in accordance with an embodiment.

In a further embodiment illustrated in FIG. 3, a single optical fibre 40 is used. The optical fibre 40 has a single core 42. The core 42 of the optical fibre 40 is modified at specific lengths to couple light out of the core, into the cladding and out of the fibre. The modifications of the core may be referred to as light-emitting regions.

In the embodiment of FIG. 3, the spacing of the modifications is approximately 1 cm.

The coupling of light 44 out of the fibre from a set of modifications 46 is shown schematically in FIG. 3.

In the embodiment of FIG. 3, the modifications 46 comprise structures with different spectral properties. Structures with different spectral properties are fabricated at different points along the fibre. The coupling of the light 44 out of the core 42 is therefore wavelength-dependent.

In the embodiment of FIG. 3, the structures 46 that are fabricated in the fibre are long period fibre Bragg gratings (LPGs). In other embodiments, the structures 46 are tilted fibre Bragg gratings. In further embodiments, the structures 46 are lines of damage which couple light into the cladding of the optical fibre. In other embodiments, any suitable fibre modifications may be used.

The modifications to the fibre could be made using a laser (for example, a femtosecond laser or UV laser. The modifications to the fibre may be made in accordance with a method described in, for example, Review of femtosecond infrared laser-induced fibre Bragg grating sensors made with a phase mask Stephen J. Mihailov, Dan Grobnic, Christopher W. Smelser, Robert B. Walker, Ping Lu and Huimin Ding Sensor Review 2011 31:4, 321-327; Donko, Y. Jung, Y. Wang, J. Hayes, S. Alam, G. Brambilla, D. Richardson, and M. Beresna, "Multicore Optical Fibre Components Fabricated Using a Femtosecond Laser Direct Writing," in Frontiers in Optics 2017, OSA Technical Digest (online) (Optical Society of America, 2017), paper FW6A.3; or H. S. Roufael, A. Quintela, M. Lomer, and J. Lopez-Higuera, "Stable at High Temperatures LPG's Inscribed by a Femtosecond Fiber Laser," in Workshop on Specialty Optical Fibers and Their Applications, OSA Technical Digest (online) (Optical Society of America, 2015), paper WT4A.19. In other embodiments, any suitable method may be used to modify the fibre core.

Laser methods may involve focusing laser illumination through the fibre cladding, to be in focus on the fibre core, to modify the core. The modification may be through non-linear processes of light absorption by the core material. Modifications may have wavelength dependent scattering properties (for example, long period fibre Bragg gratings (LPGs) or tilted fibre Bragg gratings).

Bragg gratings may be shaped to direct light in a particular direction. However, a direction of the detector 16 relative to the Bragg grating may not be known. A scattering material may be used in combination with a Bragg grating. The use of the scattering material may cause light to be emitted over a wide range of angle.

In some embodiments, the cladding of the fibre is made deliberately highly scattering to further scatter light out of the fibre cladding towards the detector 16.

In use, a light source 14 at the proximal end of the optical fibre 40 is tuned in wavelength to generate point-like sources of light at different positions along the fibre. The light source 14 may comprise any tuneable light source, for example a tuneable pulsed laser, or a pulsed white light source (for example, a supercontinuum laser) with a filter.

Injecting different wavelengths of light results in light being emitted from different ones of the modifications 46. The light emitted from the modifications 46 may be used to determine a respective location for each of the modifications 46 as described above with reference to FIGS. 1 and 2.

Using a single optical fibre may reduce or remove the need for co-packaging and careful positioning of fibres. The fabrication of the medical device may be simplified by providing multiple light-emitting regions on a single optical fibre.

Figure 4:
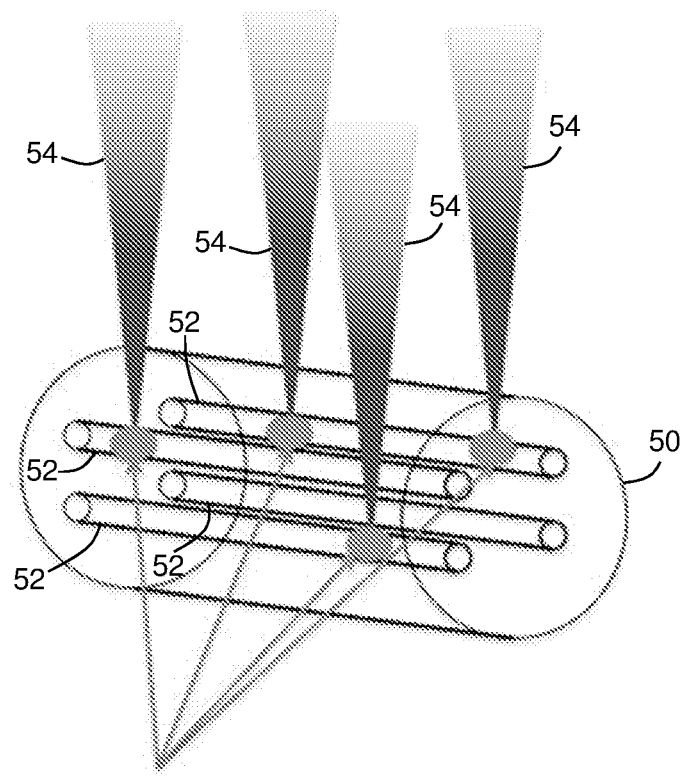
FIG. 4 is a schematic illustration of a section of a modified multicore fibre in accordance with an embodiment.

A further embodiment is illustrated in FIG. 4. In the embodiment of FIG. 4, the medical device comprises an optical fibre 50 having multiple cores 52. The individual cores 52 of the multicore optical fibre 50 are selectively modified. Different cores are modified at different points down the fibre. Each core may be modified at one or more points on the fibre.

Point-like sources of light may be generated at different positions down the fibre by exciting different cores at the proximal end, thereby outputting light through different ones of the modifications. The modifications may be referred to as light-emitting regions.

The modification of each core may be by any suitable method. For example, each modification may comprise an LPG, a tilted FBG, or core-specific damage. The modifications to the fibre may be made using a laser (e.g. femtosecond or UV). A femtosecond laser may offer the potential to modify specific cores at will across the cross section of the fibre.

The cladding of the fibre may also be made deliberately highly scattering to further scatter light out of the fibre cladding towards the detector.

The use of multiple cores may avoid the use of tuning the source wavelength. The same source wavelength may be used to illuminate all of the cores.

In some embodiments, the multicore fibre 50 comprises cores 52 that are spaced apart by a separation that is greater than the core diameter. In other embodiments, the multicore fibre 50 comprises a high density of tightly spaced cores 52, for example cores 52 having separation comparable to the core diameter.

In some embodiments, modification is targeted at one core 52. In other embodiments, modification is targeted at a region of cores 52. In some embodiments, modification is performed by scanning a laser focus across the cores 52 while the optical fibre 50 is passed under the laser modification system.

If a many core fibre is used, modification may result in a large number of modification locations along the fibre length. In some circumstances, the large number of modification locations may be considered to form a continuum of modification locations.

Illumination at the proximal end of specific cores may result in emission of light at any point along the fibre length.

Images formed from light emitted from the modification locations may be formed and processed as described above with reference to the embodiment of FIGS. 1 and 2.

In the embodiment described above with reference to FIGS. 1 to 4, light is emitted from the medical device positioned inside the body of the patient and is received by a detector positioned outside the patient. However, alternative embodiments exist in which light is emitted by a light source outside the patient and received by the medical device inside the patient.

In one such embodiment, light from a short pulse laser source is scanned across the body of a patient. For example, the light may be scanned across a two-dimensional region of the torso of a patient. A medical device is positioned inside the lung of the patient. Some light from the light source passes through the tissue of the patient and arrives in the medical device through a plurality of light-receiving regions. The light-receiving regions may comprise optical fibre tips and/or optical fibre modifications as described above.

A detector is coupled to the proximal end of the medical device (the end that is outside the patient). The detector may be, for example, a single photon detector. Photons arriving in the medical device are detected by the detector and turned into electrical signals. Their time of arrival is recorded. A position for each photon may also be determined from the position of the scanning light source at the time that photon was transmitted. Photons received from different light-emitting regions may be distinguished by, for example, the optical fibre on which they were received and/or the wavelength of light received.

Signals may be selected that correspond to ballistic photons and/or snake photons and/or photons arriving before the majority of scattered photons, for example by time gating or selecting signals in one or more time bins. The selected signals may be used to form one or more images, which is used to determine a path of the medical device using the light that was transmitted into the medical device. In some circumstances, it may be beneficial to receive photons in the dark (i.e. inside the patient). In some circumstances, noise levels may be reduced by transmitting light from the outside to the inside of the patient, rather than transmitting light from the inside to the outside of the patient.

In embodiments above, the path of a medical device in the lung of a human patient is determined. However, possible application may be much wider. A medical device may be positioned within any human or animal tissue in any suitable medical or veterinary application. For example, the medical device may be part of an endoscope that is delivered to the lungs, upper gastrointestinal tract, lower gastrointestinal tract or urinary tract of a human or animal subject. The medical device may be positioned inside any suitable organ or other tissue. In other embodiments, the medical device may be positioned inside a scattering material that does not comprise human or animal tissue.

In some embodiments, a method of locating an optical fibre using light emitted from that optical fibre (or received through the optical fibre) may be used to determine the location of a medical instrument in any one of a wide variety of medical applications.

An optical fibre for which a location is determined may be part of any suitable medical instrument, for example an endoscope or catheter delivery system. In some circumstances, the optical fibre may not be part of the medical instrument, but may be co-located with a part of the medical instrument. For example, an optical fibre may be placed in a catheter or along a guide wire. An optical fibre may be associated with any placeable device, for example any device that is to be implanted or otherwise delivered into the body. By determining a location of the optical fibre, a location of the medical instrument may also be determined. In one embodiment, the medical instrument comprises an energy source for ablation or modification of tissue.

There are many medical applications in which the location of a medical instrument positioned in the body may be determined. The methods described above may be used in any appropriate medical application, for example in training, endoscopy procedures, placement of stents or placement of catheters. For example, in training, the method of determining the location of an endoscope using light emitted from a fibre of the endoscope may be used to determine whether the endoscope has been placed correctly by the person who is training.

In current clinical practice, repeated X-rays may be used to determine the position of a device to be placed inside the body, such as a catheter. The device may be coated in a radiopaque material so that it is visible on X-rays. The repeated X-rays expose the patient to X-ray radiation. By instead using a method based on light to determine the position of the device, radiation exposure may be reduced. In some embodiments, a device path determined using light emission may be overlaid with an X-ray image of the patient.

In some circumstances, the detector 16 may be used to obtain a real-time video of a medical device, which may show the motion of the medical device as it is moved within a patient's body. The real-time video may allow a live feed to be displayed of where the medical device is located. The real-time video may be obtained without irradiation of the patient.

Obtaining a location using emitted light may increase confidence in an automated procedure that is carried out within the body, for example a robotic procedure. It may be used to ascertain that a desired location has been reached. In procedures in which tissue samples are taken, it may be used to ensure that samples are taken from the desired sample location. In procedures in which multiple samples are to be taken, it may be used to ensure that the spacing of the multiple samples is as desired.

A determined path of the medical device 10 and/or determined locations of the light-emitting regions may be overlaid on a medical image of the tissue region into which the medical device 10 is inserted. For example, an image obtained from an X-ray or CT scan may be displayed, and the determined path or locations may be overlaid on the X-ray or CT scan image. In other embodiments, other types of medical image may be used, for example images obtained from other modalities.

The medical image onto which the determined path and/or locations is overlaid may comprise anatomical information. For example, anatomical structures may be identified and/or segmented in the medical image.

The apparatuses and methods described above with reference to FIGS. 1 to 4, or apparatuses and methods as described in Tanner et al, may be used in the context of nasogastric and enteral feeding tubes. In some embodiments, dynamic time-correlated single-photon imaging may be applied to existing NG and enteral feeding tubes.

In some embodiments, time-correlated single-photon imaging is used to observe dynamic movement of a catheter in a route that follows an expected anatomy of the oesophagus in an individual subject.

Insertion of a catheter (for example, a nasogastric tube) into a subject is commenced. Pulsed light is injected into at least one optical fibre which is inserted into or forms part of the catheter. Detection of the pulsed light is used to determine a location of the catheter. The location is determined repeatedly as the insertion of the catheter is performed.

For example, in a simple embodiment, light is emitted only from a tip of an optical fibre within the catheter. A location of the point at which the light is emitted is determined and is used to determine a location of a tip of the catheter. As the catheter is inserted into the subject, the tip of the catheter moves further into the subject.

In other embodiments, light is emitted from multiple light-emitting regions of at least one optical fibre within the catheter, and locations of the multiple light-emitting regions are used to determine a path of the catheter.

The path of the catheter may be determined by determining the locations of multiple light-emitting regions along the catheter, and/or by repeatedly determining the location of one or more light-emitting regions of the catheter over time as the catheter is inserted.

The determined locations of the catheter may be compared to an expected anatomy of the subject. For example, the subject may have previously been imaged using any suitable imaging method. The route of the oesophagus in the subject may have been obtained from the previous imaging.

As described above, a determined path of the medical device 10 may be overlaid on a medical image, for example a photographic image showing anatomical features. Anatomical landmarks may be identified in the medical image. Anatomical structures may be segmented in the medical image. By comparing the determined path to the anatomy in the image, it may be determined whether the catheter is correctly placed.

If the determined locations of the catheter match the expected route of the oesophagus, it may be determined that the catheter is being correctly inserted. The repeated determination of the catheter may allow a user to observe a dynamic movement of the catheter.

In most individuals, it may be expected that the path of the oesophagus will be perpendicular from the oropharynx. A short portion of the oesophagus is behind the sternum. When a light emitter is positioned in the portion of the oesophagus is behind the sternum, it may be expected that additional scattering may occur due to the presence of high density bone. The scattering characteristics of the light received by the detector may be different when the light emitter is positioned in the portion of the oesophagus is behind the sternum from when the light emitter is positioned elsewhere in the oesophagus.

It may be intended that the tip of the catheter should exit the oesophagus in the epigastric region. It may be considered that an ideal location at which the tip of the catheter should exit the oesophagus would be below the transpyloric plane.

It may therefore be expected that a final determined location of a light emitter at the tip of the optical fibre (or, in other embodiment, an end of a determined path length) may be within the epigastric region and ideally below the transpyloric plane.

It may be expected that the path of the oesophagus (and therefore, the path of the catheter being inserted into the oesophagus) should not involve a significant lateral axial shift around the 4th intercostal space. In some cases, a significant lateral axial shift may be defined as a shift that is greater than 10 degrees.

A significant lateral axial shift around the 4th intercostal space may indicate the tracheal carina and the catheter entering the right or left main bronchi (usually at the level of the 4th thoracic vertebra, which is in line with the sternal angle, but may raise up to two vertebrae higher or lower with breathing).

Locating the path of the inserted catheter (for example, inserted nasogastric tube) may avoid ambiguity. If the catheter is incorrectly placed in the lungs when it is intended to be placed in the stomach, the final tip location of the incorrectly placed catheter could be very close to the correct location in the stomach. However, determining the path could show that the catheter was inserted through the wrong path, for example through the airways into the lungs. If the path of the catheter is substantially straight, it may be clear that no turn has occurred into the left or right main bronchi in the lungs and that the catheter has gone straight down the oesophagus.

In the embodiment described above, light is emitted from the catheter tip to observe routing dynamically.

In other embodiments, points along the length of the catheter are imaged simultaneously with light emitted from multiple discrete points along the catheter length (for example, at multiple light-emitting regions as described above with reference to FIGS. 1 to 4). In further embodiments, light is emitted uniformly along the length of the catheter.

In some embodiments, an in-built optical fibre (or group of optical fibres) is encased in the wall of the catheter. The optical fibre may be formed of glass or plastic.

In other embodiments, one or more optical fibres are fed down the catheter. The optical fibre or fibres may be formed of glass or plastic.

In some embodiments, an optical fibre is fed down the catheter in specific known incremental steps to plot the path of the catheter. The optical fibre may be fed down the catheter while the catheter is in situ, for example in the oesophagus of a patient. The feeding of the optical fibre in known steps may be achieved using, for example, a calibrated motorised fixture placed at the top of the catheter.

At each step, a location of the tip of the optical fibre is determined using light emitted from the tip of the optical fibre. The various determined tip locations are used as described above to determine a path of the catheter.

The imaging may be dynamic. The imaging may be captured such that it is possible to digitally overlay external anatomic markers on the path and the tip of the enteral feeding tube. The external anatomical markers may comprise, for example, at least one of nipples, navel, torso, sternum, epigastric region.

Anatomical triangulation may be used on a digitally produced image. A limited number of known anatomical features (for example, anatomical landmarks or external anatomical markers) may be used to label anatomical structures within the image.

The imaging of the point or points of light and the determining of the location of the catheter may be performed on as many occasions as required. The use of the method described above may allow the proximal withdrawal of a placed catheter and repositioning in situ. For example, pulsed light may be injected into one or more optical fibres of the catheter which the catheter is being withdrawn and/or repositioned. Some currently-used methods may not be able to determine catheter location during withdrawal and/or repositioning. For example, it may not be possible to perform conventional medical device location through X-ray continuously or repeatedly during repositioning since the resulting exposure to ionising radiation may be unacceptable.

Embodiments described above may describe methods that are used for NG tube insertion and monitoring, for example monitoring prior to daily feeding. The position of the NG tube may be checked during insertion. The position of the tube may be checked before each time that feeding is performed.

In other embodiments, a similar approach may be taken to any enteral feed or catheter solution with bespoke anatomical consideration and external overlay. For example, the method may be used for putting in an endotracheal tube and making sure that the endotracheal tube is not moved. The method may be used for placing an umbilical vein catheter in a newborn. The method may be used for placing a central venous line.

The methods and systems described above may contribute to a reduction in misplaced enteral feeding tubes, in particular nasogastric (NG) tubes.

The methods described may be particularly relevant in, for example, frail patients. X-ray of frail patients may be difficult. It may be difficult to position the patient. The method described may be relevant when the use of ionising radiation is to be avoided, for example in children.

In some circumstances, it may be undesirable to reinsert a nasogastric tube, for example due to difficulties in inserting. The methods described may be used to ensure that the position of the NG tube has not changed, for example after surgery to the gastrointestinal tract.

In the embodiments described above, at least one light-emitting region of at least one optical fibre is used to determine a location or path of a medical device. In other embodiments, the or each optical fibre may be replaced with any suitable waveguide. The waveguide may comprise any suitable elongate structure that is configured to guide light. The waveguide may be flexible. For example, the waveguide may be configured so as to flex along with a flexing of the medical device and/or to navigate through a channel of the medical device.

Figure 5:
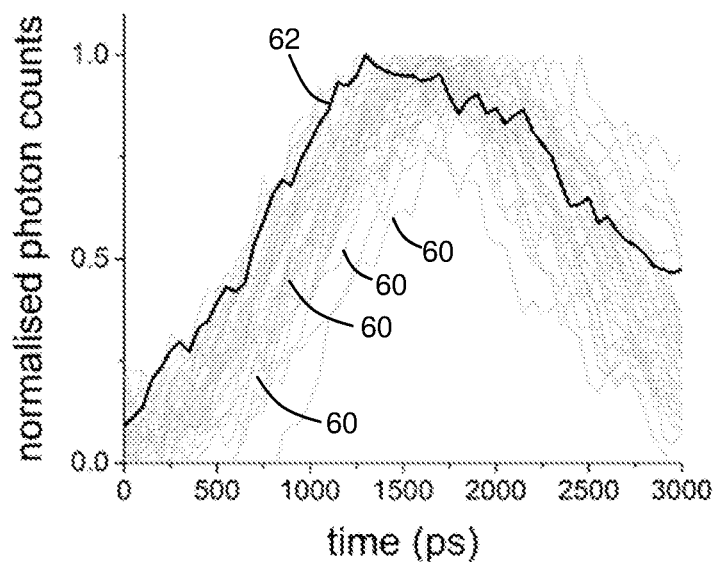
FIG. 5 is a plot of photon counts against time for a test probe placed in the lung.
Figure 6:
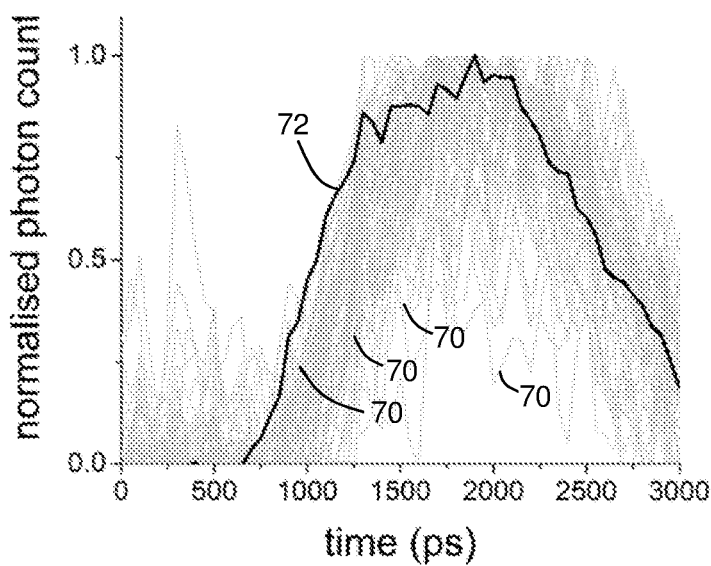
FIG. 6 is a plot of photon counts against time for a test probe placed in the stomach.

An example of photon transmission from lung and stomach in a relevant sized model is now discussed with reference to FIGS. 5 and 6. FIGS. 5 and 6 are plots showing time-resolved photon detection of light transmitted from devices placed in whole porcine cadavers (pig cadavers).

An optical fibre integrated test probe is placed in a porcine cadaver. The optical fibre integrated test probe comprises an optical fibre device having one or more light-emitting regions as described above. In the examples shown, the optical fibre integrated test probe comprises one or more individual optical fibres packaged as a single device. A 1 mm plastic sheath contains one or more 200 micrometer core fibres. Up to 5 fibres were placed in one sheath. The plastic sheath may be formed of PTFE or Pebax (polyether block amide). It is anticipated that much smaller fibres may be used in embodiments.

The distal end of each fibre is coated with a coating to produce substantially uniform emission of light in all directions. In the present example, the coating comprises titanium oxide powder mixed with epoxy glue.

Multiple fibres may be positioned so that the positions of the ends of the fibres are spaced at 1 cm intervals along the length of the test probe. In other examples, the fibres may be positioned at up to 4 cm intervals.

The optical fibre integrated test probe is deliberately placed in the lung of the porcine cadaver via a bronchoscope. The optical fibre integrated test probe is placed in the lung to emulate misplacement of a feeding tube. As described above, if a feeding tube is misplaced during insertion, it may enter the lung.

A CT scanner is used to provide an image of the porcine cadaver with the optical fibre integrated test probe in place, to confirm the device positioning in the lung.

Pulsed light is transmitted into a proximal end of the optical fibre integrated test probe. In the example shown, the pulsed light source is a laser source. An 80 MHz laser repetition rate is used, providing a 12.5 nanosecond measurement window. Pulses used are of less than 1 nanosecond or less than 100 picosecond duration. Power is less than 10 mW or less than 1 mW.

Light is emitted from the one or more light-emitting regions sequentially by individually illuminating each discrete fibre in turn. Photons are observed to exit the tissue of the porcine cadaver. Photons exiting the tissue are detected and analysed to provide a location of the optical fibre integrated test probe.

FIG. 5 shows time resolved photon detection of light transmitted from the optical fibre integrated test probe positioned in the lung, the photons having transited through the tissue structures of the porcine cadaver to the outside of the cadaver. FIG. 5 shows normalised photon counts for each of a plurality of image pixels (the multiple grey lines 60 of the plot of FIG. 5). Each line 60 on FIG. 5 may be considered to represent a record of photon arrival timing on a respective image pixel. An example of photon arrival timing on one of the image pixels of the detector is highlighted in black as line 62 of FIG. 5.

The optical fibre integrated test probe may also be deliberately placed in the stomach of the porcine cadaver via a nasogastric tube. The optical fibre integrated test probe is placed in the stomach to emulate correct placement of a feeding tube.

A CT scanner is used to provide an image of the porcine cadaver with the optical fibre integrated test probe in place, to confirm the device positioning in the stomach. Pulsed light is transmitted into a proximal end of the optical fibre integrated test probe using a light source and parameters as described above for the example in which the optical fibre integrated test probe is positioned in the lung. Light is emitted from the one or more light-emitting regions sequentially by individually illuminating each discrete fibre in turn. Photons are observed to exit the tissue. Photons exiting the tissue are detected and analysed to provide a location of the optical fibre integrated test probe.

FIG. 6 shows time resolved photon detection of light transmitted from the optical fibre integrated test probe positioned in the stomach, the photons having transited through the tissue structures of the porcine cadaver to the outside of the cadaver. FIG. 6 shows normalised photon counts for each of a plurality of image pixels (the multiple grey lines 70 of the plot of FIG. 6). Each line 70 on FIG. 5 may be considered to represent a record of photon arrival timing on a respective image pixel. An example of photon arrival timing on one of the image pixels of the detector is highlighted in black as line 72 of FIG. 6.

It may be seen that the photon arrival timing across the detector pixels when the optical fibre integrated test probe is placed in the stomach (FIG. 6) differs from the photon arrival timing across the detector pixels when the optical fibre integrated test probe is placed in the lung (FIG. 5). The photon arrival timings may be used to distinguish different placements of the optical fibre integrated test probe.

Although specific embodiments are described above, features of any of the embodiments may be combined with features of any other of the embodiments. For example, features of an embodiment in which light is transmitted from the medical device may be combined with feature of an embodiment in which light is received by the medical device. Features of any of the different medical devices described may be combined. Features described in the context of enteral tubes may be applied to any other anatomy (and vice versa).

It may be understood that the present invention has been described above purely by way of example, and that modifications of detail can be made within the scope of the invention.

Each feature disclosed in the description and (where appropriate) the claims and drawings may be provided independently or in any appropriate combination.

The invention claimed is:

1. A system comprising:
a medical device configured to be positioned at least partially within a scattering medium that forms at least a part of a body of a human or animal subject, the medical device comprising at least one optical fibre or other waveguide having a plurality of light-emitting regions arranged along at least part of the length of the at least one optical fibre or other waveguide;
a pulsed light source configured to transmit pulsed light into a proximal end of the at least one optical fibre or other waveguide, such that the pulsed light is guided along the at least one optical fibre or other waveguide to the light-emitting regions and emitted by the light-emitting regions outwards from the medical device and into the scattering medium that forms at least part of the body of the human or animal subject;
at least one single-photon detector configured to receive photons of the pulsed light that have passed through the scattering medium and generate an electrical signal corresponding to each received photon, wherein the generated electrical signals comprise electrical signals corresponding to received ballistic and scattered photons; and
a processor configured to:
select signals corresponding to at least some of the received photons based on at least a time of arrival of the received photons at the at least one single-photon detector, wherein the time of arrival of each photon comprises a difference between a time at which the photon was received at the at least one single-photon detector and a time at which a pulse of light was emitted by the pulsed light source, wherein the selecting of the signals comprises selecting signals having a time of arrival within a time interval;
determine a respective location of each of the light-emitting regions based on the selected signals; and
determine a path of at least part of the medical device based on the determined locations, wherein the determining of the location of each of the light-emitting regions based on the selected signals comprises forming at least one image using the selected signals, and determining the location of each of the light-emitting regions based on the at least one image.

2. A system according to claim 1, wherein the selecting of the signals comprises:
selecting a first set of signals having a time of arrival in a first time interval; selecting a second set of signals having a time of arrival in a second time interval; and
comparing the first set of signals with the second set of signals.

3. A system according to claim 1, wherein the determining of the location of each of the light-emitting regions based on the selected signals comprises forming at least one image using the selected signals, and determining the location of each of the light-emitting regions based on the at least one image.

4. A system according to claim 3, wherein the at least one image comprises a respective image for each of the light-emitting regions, and the determining of the location of each light-emitting region is based on the image for that light-emitting region.

5. A system according to claim 1, wherein the determining of the path of the at least part of the medical device comprises applying shape-based image processing techniques using an expected shape of the medical device and/or an expected shape of the at least one optical fibre or other waveguide.

6. A system according to claim 1, wherein the scattering medium comprises at least part of a body of a human or animal subject.

7. A system according to claim 6, wherein the processor is further configured to compare the determined location of the medical device to an expected anatomy of the human or animal subject.

8. A system according to claim 7, wherein the comparing of the location of the medical device to the expected anatomy of the subject comprises determining a location of the medical device relative to at least one of: an oesophagus of the subject, bronchi of the subject, a transpyloric plane of the subject, intercostal spaces of the subject, vertebrae of the subject.

9. A system according to claim 1, wherein the light-emitted regions are regularly spaced along the length of at least part of the at least one optical fibre or other waveguide.

10. A system according to claim 1, wherein the at least one optical fibre comprises a plurality of optical fibres, and each of the light-emitting regions comprises a tip of a respective one of the plurality of optical fibres.

11. A system according to claim 1, wherein each of the light-emitting regions is configured to transmit and/or scatter different wavelengths of light.

12. A system according to claim 1, wherein each of the light-emitting regions comprises at least one of a long-period fibre Bragg grating, a tilted fibre Bragg grating, a region of core damage.

13. A system according to claim 1, wherein the transmitting of the pulsed light into the scattering medium comprises individually illuminating each of the light-emitting regions in turn.

14. A system according to claim 1, wherein the medical device comprises an endoscope.

15. A system according to claim 1, wherein the medical device comprises a tube.

16. A system according to claim 15, wherein the optical fibre or other waveguide is positioned in a lumen of the tube.

17. A system according to claim 15, wherein the optical fibre or other waveguide is integrated into tubing material of the tube.

18. A method for determining a path of at least part of a medical device, the medical device comprising at least one optical fibre or other waveguide having a plurality of light-emitting regions arranged along at least part of the length of the at least one optical fibre, and the method comprising:
- positioning the medical device at least partially within a scattering medium that forms at least part of a body of a human or animal subject;
- transmitting pulsed light into the at least one optical fibre or other waveguide, such that the pulsed light is guided along the at least one optical fibre or other waveguide to the light-emitting regions and emitted by the light-emitting regions outwards from the medical device and into the scattering medium that forms at least part of the body of the human or animal subject;
- receiving by at least one single photon detector photons of the pulsed light that have passed through the scattering medium and generate an electrical signal corresponding to each received photon, wherein the generated electrical signals comprise electrical signals corresponding to received ballistic and scattered photons;
- selecting signals corresponding to at least some of the received photons;
- determining a respective location of each of the light-emitting regions based on the selected signals based on at least a time of arrival of the received photons at the at least one single-photon detector, wherein the time of arrival of each photon comprises a difference between a time at which the photon was received at the at least one single-photon detector and a time at which a pulse of light was emitted by the pulsed light source, wherein the selecting of the signals comprises selecting signals having a time of arrival within a time interval, wherein the determining of the location of each of the light-emitting regions based on the selected signals comprises forming at least one image using the selected signals, and determining the location of each of the light-emitting regions based on the at least one image; and
- determining a path of at least part of the medical device within the body of the human or animal subject based on the determined locations.

19. A computer program product comprising computer-readable instructions that are executable by a processor to select signals corresponding to received photons of pulsed light that have passed through a scattering medium that forms at least part of the body of the human or animal subject, to determine a respective location of each of plurality of light-emitting regions based on the selected signals, wherein the determining of the location of each of the light-emitting regions based on the selected signals comprises forming at least one image using the selected signals, and determining the location of each of the light-emitting regions based on the at least one image, and to determine a path of a medical device based on the determined locations, wherein the photons are received by at least one single-photon detector configured to receive photons of the pulsed light that have passed through the scattering medium and generate an electrical signal corresponding to each received photon, wherein the generated electrical signals comprise electrical signals corresponding to received ballistic and scattered photons, and wherein the selection of signals is based on at least a time of arrival of the received photons at the at least one single-photon detector, wherein the time of arrival of each photon comprises a difference between a time at which the photon was received at the at least one single-photon detector and a time at which a pulse of light was emitted by the pulsed light source, wherein the selecting of the signals comprises selecting signals having a time of arrival within a time interval.

20. A system comprising:
- a medical device configured to be positioned at least partially within a scattering medium that forms at least part of a body of a human or animal subject, the medical device comprising at least one optical fibre or other waveguide having a plurality of light-receiving regions arranged along at least part of the length of the at least one optical fibre or other waveguide, such that light is received at the light-receiving regions form the scattering medium that forms at least part of the body of the human or animal subject;
- a pulsed light source configured to be positioned external to the scattering medium and to transmit pulsed light into the scattering medium;
- at least one single-photon detector coupled to a proximal end of the at least one optical fibre or other waveguide, wherein the at least one single-photon detector is configured to receive photons of the pulsed light that have passed through the scattering medium and been received through the light-receiving regions and guided along the at least one optical fibre or other waveguide to the at least one detector and generate an electrical signal corresponding to each received photon, wherein the generated electrical signals comprise electrical signals corresponding to received ballistic and scattered photons; and
- a processor configured to:
- select signals corresponding to at least some of the received photons based on at least a time of arrival of the received photons at the at least one single-photon detector, wherein the time of arrival of each photon comprises a difference between a time at which the photon was received at the at least one single-photon detector and a time at which a pulse of light was emitted by the pulsed light source, wherein the selecting of the signals comprises selecting signals having a time of arrival within a time interval;
- determine a respective location of each of the light-receiving regions based on the selected signals wherein the determining of the location of each of the light-emitting regions based on the selected signals comprises forming at least one image using the selected signals, and determining the location of each of the light-emitting regions based on the at least one image; and
- determine a path of at least part of the medical device within the body of the human or animal subject based on the determined locations.

21. A system according to claim 20, wherein the transmitting of the pulsed light into the scattering medium comprises varying a position of the light source with respect to the scattering medium and/or varying an incident position of the pulsed light from the light source on the scattering medium.

22. A method comprising:
   positioning a medical device at least partially within a scattering medium that forms at least part of a body of a human or animal subject, the medical device comprising at least one optical fibre or other waveguide having a plurality of light-receiving regions arranged along at least part of the length of the at least one optical fibre or other waveguide, such that light is received at the light-receiving regions from the scattering medium that forms at least part of the body of the human or animal subject;
   positioning a pulsed light source external to the scattering medium;
   transmitting pulsed light from the pulsed light source into the scattering medium that forms at least part of the body of the human or animal subject;
   receiving, by at least one single-photon detector coupled to a proximal end of the at least one optical fibre or other waveguide, photons of the pulsed light that have passed through the scattering medium that forms at least part of the body of the human or animal subject and been received through the light-receiving regions and guided along the at least one optical fibre or other waveguide to the at least detector medium and generate an electrical signal corresponding to each received photon, wherein the generated electrical signals comprise electrical signals corresponding to ballistic and scattered photons;
   selecting signals corresponding to at least some of the received photons based on at least a time of arrival of the received photons at the at least one single-photon, wherein the time of arrival of each photon comprises a difference between a time at which the photon was received at the at least one single-photon detector and a time at which a pulse of light was emitted by the pulsed light source, wherein the selecting of the signals comprises selecting signals having a time of arrival within a time interval;
   determining a respective location of each of the light-receiving regions based on the selected signals;
   determining a path of at least part of the medical device within the body of the human or animal subject based on the determined locations; and
   wherein the determining of the location of each of the light-emitting regions based on the selected signals comprises forming at least one image using the selected signals, and determining the location of each of the light-emitting regions based on the at least one image.

23. A system comprising:
   an enteral tube configured to be positioned at least partially inside the body of a human or animal subject, wherein the enteral tube comprises or at least partially contains at least one optical fibre or other waveguide, the at least one optical fibre or other waveguide comprising at least one light-emitting region;
   a pulsed light source configured to transmit pulsed light into a proximal end of the at least one optical fibre or other waveguide, such that the pulsed light is guided along the at least one optical fibre or other waveguide to the light-emitting region or regions and emitted by the light-emitting region or regions outwards from the enteral tube and into the body of the subject;
   at least one single-photon detector configured to receive photons of the pulsed light that have passed through the body of the subject and generate an electrical signal corresponding to each received photon, wherein the generated electrical signals comprise electrical signals corresponding to ballistic and scattered photons; and
   a processor configured to:
      select signals corresponding to at least some of the received photons based on at least a time of arrival of the received photons at the at least one single-photon detector, wherein the time of arrival of each photon comprises a difference between a time at which the photon was received at the at least one single-photon detector and a time at which a pulse of light was emitted by the pulsed light source, wherein the selecting of the signals comprises selecting signals having a time of arrival within a time interval;
      determine a location of the or each light-emitting region based on the selected signals; and
      determine a location of the enteral tube within the body of the human or animal subject based on the determined location or locations, wherein the determining of the location of each of the light-emitting regions based on the selected signals comprises forming at least one image using the selected signals, and determining the location of each of the light-emitting regions based on the at least one image.

* * * * *